United States Patent [19]

Graboyes

[11] 4,107,179
[45] Aug. 15, 1978

[54] METHOD FOR PREPARING TICRYNAFEN

[75] Inventor: Harold Graboyes, Overbrook Hills, Pa.

[73] Assignee: SmithKline Corporation, Philadelphia, Pa.

[21] Appl. No.: 826,604

[22] Filed: Aug. 22, 1977

[51] Int. Cl.² .............................................. C07D 333/24
[52] U.S. Cl. .............................................. 260/332.2 A
[58] Field of Search ................................. 260/332.2 A

[56] References Cited

U.S. PATENT DOCUMENTS

| | | | |
|---|---|---|---|
| 3,758,506 | 9/1973 | Godfroid | 260/332.2 A |
| 4,017,632 | 4/1977 | Thuillier | 260/332.2 A |

*Primary Examiner*—A. Siegel
*Attorney, Agent, or Firm*—William H. Edgerton

[57] ABSTRACT

A new method for preparing ticrynafen comprises reacting 2,3-dichloro-4-hydroxyphenyl-2-thienylmethanone with an alkali metal salt of chloro or bromo acetic acid in aqueous solvent. An advantageous aspect of the reaction is that yields are increased with the addition of an alkali metal iodide to the reaction mixture.

5 Claims, No Drawings

METHOD FOR PREPARING TICRYNAFEN

This invention comprises a new chemical method for preparing the diuretic agent ticrynafen (tienilic acid) which offers high yields but efficient low cost use of chemical ingredients and equipment. The basic elements of the process may be described as follows:

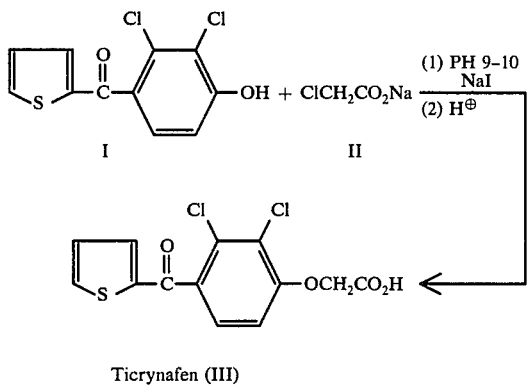

Ticrynafen (III)

PRIOR ART STATEMENT

U.S. Pat. No. 3,758,506 describes the preparation of ticrynafen by reacting 2,3-dichloro-4-hydroxyphenyl-2-thienylmethanone (I) with ethylchloroacetate in sodium ethylate/ethanol. The ester form was obtained which necessitated a subsequent hydrolysis step to obtain ticrynafen. Thuillier et al., *Eur. J. Med. Chem.* 9(6), 625 (1974) describes the reaction of a heterocyclic containing phenol similar to I above with "the acid or the α-halogenoacetic ester in an aqueous or alcohol medium in the presence of a base". The only example in the latter publication with a thenoyl intermediate (I above) is using sodium and ethanol to give the ester.

I have now found that the phenolic compound (I) will condense with the alkali metal salt of chloroacetic or bromoacetic acid in good yields and under simple reaction conditions. The reaction is most conveniently run by reacting the phenol (I) with an equimolar amount, or an excess, of sodium or potassium chloroacetate in an aqueous solvent in the presence of alkali sufficient to form the salt of the phenol and maintain the pH of the reaction mixture at about 9-10. The solvent is most conveniently water. Most conveniently the reaction is run at moderately high temperatures such as from about 90-95° C. for about 3-6 hours. The reaction will proceed as well at lower temperatures but using longer periods of time. Longer periods of reaction gave no significant advantage.

A particularly advantageous aspect of this reaction is that the addition of an alkali metal iodide during the reaction increases the yield from about 80% to almost quantitative yield. In addition the process of this invention gives a reaction product which is very easy to isolate and purify by methods known in the art. Of course either sodium or potassium iodide can be used; however, one skilled in the art will recognize that it is desirable to employ the same cation for the hydroxide and iodide reagents. The iodide is most conveniently used in amount of from about 1 to 15% by weight, preferably about 2.5-10%, of the phenolic starting material.

Of course in the reaction described above the sodium salt of ticrynafen is obtained. The free acid form is obtained by neutralization by methods known to the art such as treatment in water with a mineral acid such as sulfuric or hydrohalic acid.

The process of this invention gives excellent yields such as quantitative for the crude product to 90–95% of purified ticrynafen. No expensive or noxious organic chemicals are used in the reaction step and a high throughput is practical.

The following example will illustrate this invention. Other modifications of this invention will be apparent from this description.

EXAMPLE 1

A reaction flask was charged with 1092 g. (4.0 mole) of 2,3-dichloro-4-hydroxyphenyl-2-thienylmethanone (U.S. Pat. No. 3,758,506), 160 g. (4.0 mole) of sodium hydroxide powder, 100 g. of sodium iodide granules and 1400 ml. of water. The mixture was heated to 90–95° C. and a mixture of 1400 g. (12.0 mole) of sodium chloroacetate in 2800 ml. of water was added over 3 hours while the pH was maintained at 9.0–10.0 using 10N sodium hydroxide solution. After addition the reaction mixture was heated with maintenance of pH for 3 additional hours.

The slurry was cooled. The product was separated and washed with 1N sodium hydroxide solution. After drying a 98.7% yield of the sodium salt was obtained.

The salt, wet or dry, was suspended in 7.5 l. of water at 70°–75° C. Sulfuric acid (1 Kg. conc. + 800 ml. of water) was added over the period of 1 hour and the mixture was stirred another hour. The white slurry was cooled and the crude acid separated, washed with water and dried (1288 g., 97.3%).

The crude acid is recrystallized from dichloroethane with activated charcoal to give 1205.5 g. (91%) of ticrynafen.

The potassium salts may be substituted in this procedure as may bromoacetate or other lower alkyl esters in place of the haloacetates.

What is claimed is:

1. The method of preparing ticrynafen having the formula:

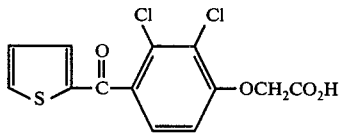

or its sodium or potassium salts comprising reacting a phenolic compound of the formula:

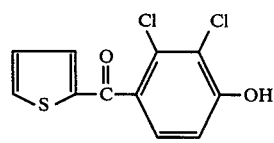

with sodium or potassium chloroacetate in an aqueous solvent at about 90°–95° C. at a pH of about 9–10 in the presence of sodium or potassium iodide in the amount of about 1–15% by weight of said phenolic compound to give the sodium or potassium salt of ticrynafen and optionally reacting said salt product with acid to obtain the acid form.

2. The method of claim 1 in which sodium hydroxide to control the pH, sodium chloroacetate and sodium iodide are used.

3. The method of claim 1 in which potassium hydroxide to control the pH, potassium chloroacetate and potassium iodide are used.

4. The method of claim 2 in which the amount of iodide is about 10% of the phenolic starting material.

5. The method of claim 3 in which the amount of iodide is about 10% of the phenolic starting material.

* * * * *